(12) United States Patent
Breivik et al.

(10) Patent No.: US 9,301,536 B2
(45) Date of Patent: Apr. 5, 2016

(54) ANTIOXIDANT COMPOSITION FOR MARINE OILS COMPRISING TOCOPHEROL, ROSEMARY EXTRACT, ASCORBIC ACID AND GREEN TEA EXTRACT

(75) Inventors: Harald Breivik, Porsgrunn (NO); Charlotte Jacobsen, Tastrup (DK); Vidar Moen, Skien (NO); Tanja Vojnovic, Siljan (NO)

(73) Assignee: Epax Norway AS (NO)

( * ) Notice: Subject to any disclaimer, the term of this patent is extended or adjusted under 35 U.S.C. 154(b) by 1361 days.

(21) Appl. No.: 13/060,238

(22) PCT Filed: Aug. 26, 2009

(86) PCT No.: PCT/NO2009/000300
§ 371 (c)(1),
(2), (4) Date: May 23, 2011

(87) PCT Pub. No.: WO2010/033034
PCT Pub. Date: Mar. 25, 2010

(65) Prior Publication Data
US 2011/0212183 A1 Sep. 1, 2011

(30) Foreign Application Priority Data
Sep. 19, 2008 (NO) .................................. 20083997

(51) Int. Cl.
| | |
|---|---|
| *A23D 9/06* | (2006.01) |
| *A61K 36/82* | (2006.01) |
| *A61K 36/53* | (2006.01) |
| *A61K 35/60* | (2006.01) |
| *C11B 5/00* | (2006.01) |

(52) U.S. Cl.
CPC . *A23D 9/06* (2013.01); *A61K 35/60* (2013.01); *A61K 36/53* (2013.01); *A61K 36/82* (2013.01); *C11B 5/0021* (2013.01); *C11B 5/0085* (2013.01)

(58) Field of Classification Search
None
See application file for complete search history.

(56) References Cited

U.S. PATENT DOCUMENTS

| | | | |
|---|---|---|---|
| 5,102,659 A | 4/1992 | Hudson | |
| 6,231,877 B1 | 5/2001 | Vacher et al. | |
| 7,771,752 B2 * | 8/2010 | Bartlett et al. ................ | 424/523 |
| 2005/0048143 A1 | 3/2005 | McAnalley et al. | |
| 2005/0123667 A1 | 6/2005 | Sakuma et al. | |
| 2007/0190114 A1 | 8/2007 | Smart | |

FOREIGN PATENT DOCUMENTS

| | | | |
|---|---|---|---|
| EP | 0612346 B1 | | 6/1995 |
| EP | 1897530 A1 | | 3/2008 |
| EP | 1952796 A1 | | 8/2008 |
| JP | 2003-092988 A | | 4/2003 |
| JP | 2006193713 A | * | 7/2006 |
| WO | WO-94/22322 A1 | | 10/1994 |
| WO | WO-02/34072 A2 | | 5/2002 |
| WO | WO-2006/056293 A1 | | 6/2006 |
| WO | WO-2007/021789 A1 | | 2/2007 |

OTHER PUBLICATIONS

"Fish Oil, Rich in Omega-3-Acids", *European Pharmacopoeia 5.0*, (Monograph No. 1912), (2008), 1595-1598.
International Application Serial No. PCT/NO2009/000300, International Preliminary Report on Patentability completed Dec. 20, 2010, 9 pgs.
International Application Serial No. PCT/NO2009/000300, International Search Report mailed Dec. 30, 2009, 4 pgs.
Norwegian Application Serial No. 20083997, Search Report, (2009), 1 pg.
Chu, Y.-H., et al., "Effects on antioxidants on peanut oil stability", *Food Chemistry, 66*, (1999), 29-34.
Yanishlieva, N. V., et al., "Stabilisation of edible oils with natural antioxidants", *Eur. J. Lipid Sci. Technol., 103*, (2001), 752-767.
"European Application Serial No. 09814832, Supplementary European Search Report dated Oct. 13, 2011", 1 pg.

* cited by examiner

*Primary Examiner* — Susan Hoffman
(74) *Attorney, Agent, or Firm* — Schwegman Lundberg & Woessner, P.A.

(57) ABSTRACT

The present invention relates to compositions suitable for improving oxidative stability of marine oils, marine oils having improved oxidative stability as well as methods for manufacturing such compositions.

16 Claims, 2 Drawing Sheets

ANTIOXIDANT COMPOSITION FOR MARINE OILS COMPRISING TOCOPHEROL, ROSEMARY EXTRACT, ASCORBIC ACID AND GREEN TEA EXTRACT

RELATED APPLICATIONS

This application is a nationalization under 35 U.S.C. 371 of PCT/NO2009/000300, filed Aug. 26, 2009 and published as WO 2010-033034 on Mar. 25, 2010, which claimed priority to Norwegian Patent Application No. 20083997, filed Sep. 19, 2008; which applications and publication are incorporated herein by reference in their entirety.

FIELD OF THE INVENTION

The present invention relates to compositions suitable for improving oxidative stability of marine oils, marine oils having improved oxidative stability as well as methods for manufacturing such compositions.

BACKGROUND OF THE INVENTION

Omega-3 fatty acids are considered essential fatty acids, which means that they are essential to human health but cannot be synthesised by the human body. For this reason, omega-3 fatty acids must be obtained through the diet.

The European Pharmacopoeia defines the omega-3 fatty acids as the following acids (see for example Monograph no. 1912, Fish Oil, Rich in Omega-3-Acids): alpha-linolenic acid (C18:3 n-3; ALA), moroctic acid (C18:4 n-3), eicosatetraenoic acid (C20:4 n-3), eicosapentaenoic (timnodonic) acid (C20:5 n-3; EPA), heneicosapentaenoic acid (C21:5 n-3), docosapentaenoic (clupanodonic) acid (C22:5 n-3) and docosahexaenoic (cervonic) acid (C22:6 n-3; EPA). Omega-3 fatty acids with chain-length of 20 and above are called long-chain omega-3 fatty acids. ALA is common in a number of vegetable oils. C18:4 n-3 is available from fish oils, as well as from some vegetable oils. Once eaten, the body can to some extent convert ALA and C18:4 n-3 to the long-chain omega-3 fatty acids, including EPA and DHA. However, fish oil and other marine oils are known to be the best source of these omega-3 fatty acids. Long-chain omega-3 fatty acids can also be obtained via fermentation of single cell oils (microbial oils), and research projects aim at producing EPA and DHA via gene-modified terrestrial plants.

Omega-3 fatty acids have been demonstrated to reduce the risk of coronary heart disease as well as having a positive effect on children's development, as well as on the skin. Results have also been disclosed indicating the positive effect of these fatty acids on certain mental illnesses, autoimmune diseases and joint complaints. There are therefore many reasons for considering taking fish oil as a valuable dietary supplement, including the long-term effect which this dietary supplement is now thought to have.

However, fish oils and especially concentrates of omega-3 fatty acids are very susceptible to oxidation. Oxidation limits the use of such products in food applications, and also limits oral administration of omega-3 containing nutritional supplements, except where the supplements are encapsulated.

Microencapsulation is a way of formulating omega-3 oils for food applications. However, microencapsulated products are relatively expensive, the encapsulation material often takes up more volume than the oil, so that the total volume becomes impractical to handle, and also there might be doubts whether the encapsulation material prevents the valuable omega-3 fatty acids from being absorbed in the intestinal tract.

An alternative to microencapsulation is the use of antioxidants in the oil to slow down oxidation. Most antioxidants interfere with the propagation of lipid oxidation by donating a hydrogen atom to, and thereby inactivating, chain-carrying peroxyl radicals and/or alkoxyl radicals. Hence, after breaking the chain reaction of lipid peroxidation, an antioxidant is itself converted to a radical. To be effective, the antioxidant radical has to be sufficiently stable so as to react slowly with the lipid substrate and rapidly with lipid peroxyl radicals and/or alkoxyl radicals. Several natural and synthetic compounds fulfil this condition and are widely used for preserving polyunsaturated fatty acids (PUFA) from oxidative deterioration. Even though a number of synthetic antioxidants have been extensively used for the stabilization of foods, much interest has developed in the use of naturally occurring antioxidants because of the adverse attention received by the synthetic antioxidants and because of the worldwide trend to avoid or minimize the use of synthetic food additives.

Tocopherols are among the most important lipid-soluble natural antioxidants, and appear to be the major physiological scavengers of free radicals inside human membranes and plasma lipids. The fact that these compounds are naturally occurring lipid-soluble antioxidants make them particularly useful in combination with marine oils, having high amounts of PUFA, intended for human consumption (Free radical biology & medicine, 2005, vol. 38, page 78-84; J. Chem. Soc., Perkin Trans. 2, 1998).

Another example of antioxidants commonly used in combination with marine oils are rosemary extracts. The antioxidant potential of such an extract has previously been tested on cod liver oil and has been shown to have significantly higher antioxidant effect compared with seven other naturally occurring antioxidants (Journal of Aquatic Food Product Technology; vol. 14; 2005; page 75-94). Further, a mixture of α-tocopherol and rosemary extract has previously been shown to exert very strong antioxidant activity in sardine oil, where their combination not only inhibited the formation of hydroperoxides much more effectively than when present separately but the activity of tocopherol was retained for a longer period of time (Yukagaku 1994, vol. 43, no 2, page 109-115).

Ascorbyl palmitate is an ester formed from ascorbic acid and palmitic acid. In addition to its use as a source of vitamin C, it is also commonly used as an antioxidant food additive. The compound is difficult to dissolve in oil formulations, and it is therefore common to add lecithin to the antioxidant preparation in order to solubilise the ascorbyl palmitate (EP612346). Even though lecithin is commonly regarded as a well-tolerated and non-toxic surfactant, lecithin may contain traces of proteins and for this reason has to be declared as a potential allergen in nutritional supplements. Producers and distributors prefer to avoid components that might act as allergens.

In addition to traditional and cultural reasons for consuming tea, a renewed interest has been fuelled by the discovery of strong antioxidant properties provided by tea prepared from *Camellia Sinensis* leaves (green tea). Such an antioxidant effect has primarily been attributed to the polyphenol content of the tea leaves, commonly known as tea catechins. Said catechins are water-soluble and therefore not easily dissolvable in oil formulations. In order to make these strong antioxidants lipid-soluble, it has been suggested to derivatise part of the phenols with fatty acid (WO07021789). An unwanted side effect of derivatising these compounds with fatty acids is that the intestinal absorption of these compounds increases significantly. Polyphenols from green tea are generally not absorbed into the body, and the increased absorption of these compounds add a problem from a regulatory point of view.

Even though a number of antioxidants and various combinations thereof have been disclosed (e.g. U.S. Pat. No. 5,102,659), there is still a need for additional antioxidant compositions having improved characteristics.

SUMMARY OF THE INVENTION

As previously disclosed, ascorbyl palmitate is very effective in slowing down oxidation of lipids in a marine oil. In order to dissolve this compound in oil formulations, it is common to add lecithin. However, producers and distributors prefer to avoid components such as lecithin, since such products has to be declared as a potential allergen.

Accordingly, it is an object of the present invention to provide a composition comprising a marine oil and ascorbic acid and/or an ascorbic acid derivative, such as e.g. ascorbyl palmitate, without the need of adding lecithin.

Further, it is previously known that green tea extracts have strong antioxidant activity. However, most of the compounds responsible for said antioxidant activity are water-soluble and therefore not easily dissolvable in oil formulations. It has been suggested to derivatise the active compounds with fatty acids, but since this may add a problem from a regulatory point of view, it is desirable to avoid this strategy.

Accordingly, it is an object of the present invention to provide a composition comprising a marine oil and green tea extract without having to chemically modify the green tea catechines.

The present invention relates to a simple method for increasing the solubility of said two components, ascorbic acid and/or an ascorbic acid derivative such as e.g. ascorbyl palmitate and green tea extracts, in a marine oil which makes it possible to prepare a marine oil composition having improved oxidation stability without having to introduce potentially allergenic substances, such as lecithin, and without having to chemically modify the green tea catechins.

Further, the inventors of the present invention have found a synergistic antioxidative effect from combining a mixture of tocopherols, rosemary extract and ascorbyl palmitate with green tea extract.

A first aspect of the present invention relates to a composition suitable for improving oxidation stability of a marine oil, comprising at least one tocopherol and/or tocopherol derivative, rosemary extract or an active fraction thereof, ascorbic acid and/or an ascorbic acid derivative and green tea extract or an active fraction thereof.

A second aspect of the present invention relates to a composition comprising a marine oil and the composition according to the first aspect of the present invention.

A third aspect of the present invention relates to a method for manufacturing the composition according to the second aspect of the present invention, the method comprising the following steps:
a) ascorbic acid and/or a derivative thereof is mixed with a small amount of oil;
b) green tea extract or an active fraction thereof is mixed with the marine oil;
c) the mixture obtained in step b) is filtered through a filter having a pore size in the range 0.1-100 μm.
d) the at least one tocopherol and/or tocopherol derivative, rosemary extract or an active fraction thereof and the mixture obtained in step a) is mixed with said green tea extract before filtering or after filtering.

A fourth aspect of the present invention relates to a nutritional, food or pharmaceutical composition, comprising the composition according to the invention.

Preferred embodiments of the present invention are set forth in the accompanying dependent claims.

DETAILED DESCRIPTION OF THE INVENTION

Figure 1:
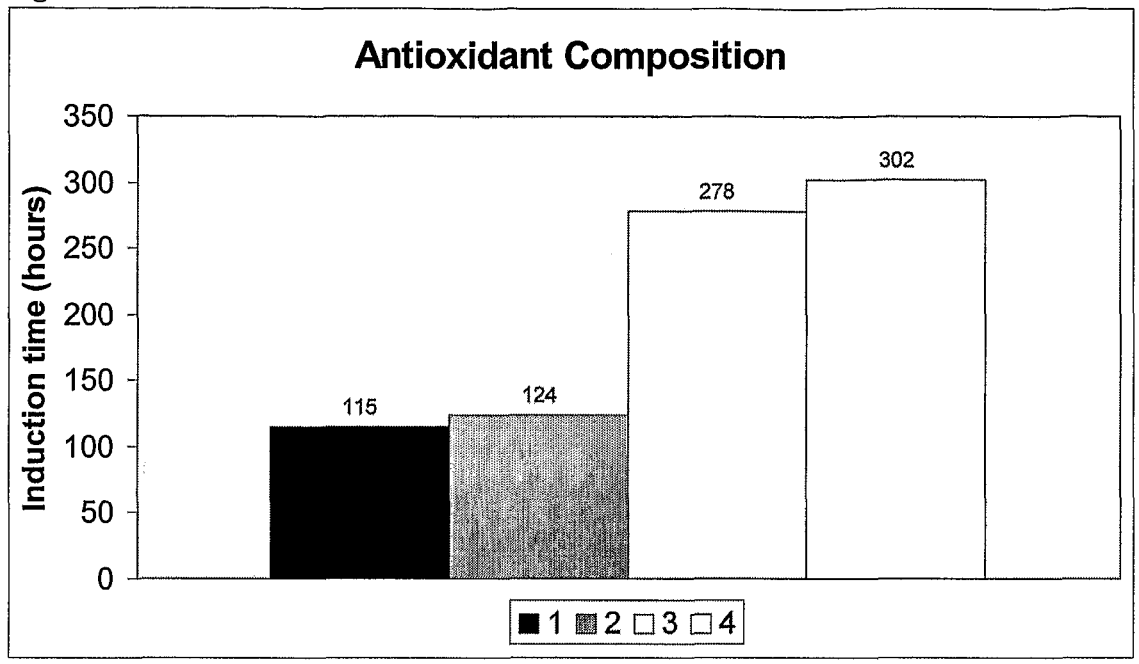
FIG. 1 shows a synergistic antioxidative effect (induction time analysis) from combining a mixture of tocopherols (Tocoblend L 70 IP, Vitablend (1.03 mg per gram marine oil)), rosemary extract (Oleoresin Rosemary, Kalsec (2.87 mg per gram marine oil)) and ascorbyl palmitate (Grindox ascorbyl palmitate, Danisco (0.72 mg per gram marine oil)) and olive oil (0.78 mg olive oil per gram marine oil) with green tea extract (GUARDIAN™ Green Tea Extract 20M, Danisco (5.4 mg per gram marine oil before filtration).
1 represents Ascorbyl Palmitate+Tocopherols+Rosemary extract;
2 represents Green Tea Extract;
3 represents 1+2, "filtration, 20° C.";
4 represents 1+2, "filtration, 80° C."

As previously disclosed, there are many reasons for considering taking fish oil as a valuable dietary supplement, including the long-term effect which this dietary supplement is now thought to have. However, fish oils and especially concentrates of omega-3 fatty acids are very susceptible to oxidation. Accordingly, there is a need in the art to provide marine oil composition having improved oxidative stability.

It has previously been disclosed that green tea extracts contain compounds which have strong antioxidant activity. However, most of the compounds responsible for said antioxidant activity are water-soluble and therefore not easily dissolvable in oil formulations. It has been suggested to derivatise the active compounds with fatty acids (WO07021789), but since this may add a problem from a regulatory point of view, it is desirable to avoid this strategy.

Surprisingly, the inventors of the present invention discovered that if a mixture of green tea extract and a marine oil is filtered using a filter having a pore size in the range 15-40 µm, the oil appeared totally clear with no visible particles and showed a significantly increased stability (example 1 and example 2).

Further, it has previously been disclosed that ascorbyl palmitate is very effective in slowing down oxidation of lipids in marine oils. However, in order to dissolve this compound in oil formulations it is common to add lecithin, a compound which producers and distributors prefer to avoid since it has to be declared as a potential allergen.

Surprisingly, it has now been found that if said ascorbyl palmitate, preferably ground or milled ascorbyl palmitate, is premixed with a small amount of oil, preferably an oxidative stable oil (e.g. olive oil), the product is easily dissolvable in a marine oil.

Thus, one aspect of the present invention relates to a method for manufacturing a composition comprising a marine oil having improved oxidation stability, the method comprising the following steps:
a) ascorbic acid and/or a derivative thereof is mixed with a small amount of oil, wherein said oil preferably is an oxidative stabile oil, such as a vegetable oil, e.g. olive oil such as food grade olive oil;
b) green tea extract or an active fraction thereof is mixed with the marine oil;
c) the mixture obtained in step b) is filtered through a filter having a pore size in the range 0.1-100 µm.
d) the at least one tocopherol and/or tocopherol derivative, rosemary extract or an active fraction thereof and the mixture obtained in step a) is mixed with said green tea extract before filtering or after filtering.

Preferably, said ascorbic acid and/or a derivative thereof, the at least one tocopherol and/or tocopherol derivative, rosemary extract or an active fraction thereof is mixed with said green tea extract before filtering.

Further, it is preferred that both the ascorbic acid and/or a derivative thereof, the at least one tocopherol and/or tocopherol derivative, the rosemary extract or an active fraction thereof are dissolved in a small amount of oil. Said oil is preferably an oxidative stabile oil, such as a vegetable oil, e.g. olive oil such as food grade olive oil. To facilitate this process the oily mixture may be stirred, shaken and/or treated in an ultrasonic bath at temperature in the range 10-180° C. (such as 160° C.), e.g. in the range 20-120° C. (such as 20° C.), 50-100° C. or 80-90° C. (such as 80° C.).

Said ascorbic acid and/or a derivative thereof is preferably milled or ground before it is mixed with said small amount of an oil. Further, it is preferred that the milling or grounding is as gentle as possible, e.g. by a teflon coated magnet stirrer or a similar device suitable for large scale production.

Furthermore, it is preferred that said green tea extract is milled or ground.

In one preferred embodiment according to the present invention, the mixture that is to be filtered is stirred, shaken and/or treated in an ultrasonic bath at temperature in the range 10-180° C. (such as 160° C.), e.g. in the range 20-120° C. (such as 20° C.), 50-100° C. or 80-90° C. (such as 80° C.) before said mixture is filtered through a filter having a pore size in the range 0.1-100 µm, preferably in the range 5-80 µm, more preferably in the range 10-50 µm and most preferably in the range 10-40 µm, such as 15-40 µm.

One embodiment according to the present invention relates to a method for manufacturing a composition comprising a marine oil having improved oxidation stability, the method comprising the following steps:
a) ascorbic acid and/or an ascorbic acid derivative, the at least one tocopherol and/or tocopherol derivative, rosemary extract or an active fraction thereof and a small amount of oil, preferably an oxidative stabile oil, such as a vegetable oil, e.g. olive oil such as food grade olive oil are mixed;
b) the mixture obtained in step a) and green tea extract or an active fraction thereof are mixed with the marine oil;
c) the mixture obtained in step b) is filtered through a filter having a pore size in the range 0.1-100 µm.

One preferred embodiment according to the present invention relates to a method for manufacturing a composition comprising a marine oil having improved oxidation stability, the method comprising the following steps:
a) ascorbic acid and/or an ascorbic acid derivative is milled or ground; it is preferred that the milling or grounding is as gentle as possible, e.g. by a teflon coated magnet stirrer or a similar device suitable for large scale production;
b) ascorbic acid and/or an ascorbic acid derivative obtained in step a), the at least one tocopherol and/or tocopherol derivative, rosemary extract or an active fraction thereof and a small amount of oil, preferably an oxidative stabile oil, such as a vegetable oil, e.g. olive oil such as food grade olive oil are mixed;
c) the mixture obtained in step b) is stirred, shaken and/or treated in an ultrasonic bath at temperature in the range 10-180° C., such as 160° C., e.g. in the range 20-120° C., such as 20° C., 50-100° C. or 80-90° C., such as 80° C.
d) green tea extract, or an active fraction thereof, is optionally milled or ground;
e) the preparations according to c) and green tea extract, optionally the green tea extract obtained in step d), are mixed with the marine oil;
f) the mixture obtained in step e) is stirred at a temperature in the range 10-180° C., such as 160° C., e.g. in the range 20-120° C., such as 20° C., 50-100° C. or 80-90° C., such as 80° C.;
g) the mixture obtained in step f) is filtered through a filter having a pore size in the range 0.1-100 µm, preferably in the range 5-80 µm, more preferably in the range 10-50 µm and most preferably in the range 10-40 µm, such as 15-40 µm;

By the expression "small amount of oil" there is meant that the volume of said oil is less than 1% (w/w) of the marine oil according to the present invention, preferably less than 0.1% (w/w), e.g. less than 0.01% (w/w).

Now being able to dissolve extracts from green tea in a marine oil, the inventors of the present invention have surprisingly found a synergistic antioxidative effect from combining a mixture of tocopherols, rosemary extract and ascorbyl palmitate with green tea extract.

Thus, a further aspect of the present invention relates to a composition obtainable by the above mentioned method. Such a composition comprises a composition suitable for improving oxidation stability of a marine oil which comprises at least one tocopherol and/or tocopherol derivative, rosemary extract or an active fraction thereof, ascorbic acid and/or an ascorbic acid derivative and green tea extract or an active fraction of said green tea extract; and a marine oil.

In one preferred embodiment, the composition according to the present invention does not contain lecithin. It is also preferred that said composition does not contain any synthetic emulsifiers.

By the expression "marine oil" there is meant a marine oil or an oil based on a marine oil such as a marine-based omega-3 fatty acid concentrate. Preferably, said marine oil is a fish oil or an oil based on fish oil such as a fish-based omega-3 fatty acid concentrate, e.g. EPAX 6000 TG (complies with European Pharmacopoeia monograph 1352), EPAX 6000 TG/N (complies with European Pharmacopoeia monograph 1352), EPAX 6000 EE (complies with European Pharmacopoeia monograph 2063) or similar products.

By the expression "tocopherol" there is meant not only alpha-tocopherol but also beta-, gamma- or delta-tocopherol as well as any mixture thereof. 6-hydroxy-2,5,7,8-tetramethylchroman-2-carboxylic acid is also meant to be included in said group of tocopherol compounds. Examples of useful derivatives are esters, for example, tocopherol acetate, tocopherol linoleate, tocopherol nicotinate, tocopherol sorbate, or tocopherol succinate. The amount of tocopherol used in the composition will vary depending upon the potency of the chosen substance or mixture of substances, but will generally be in the range of from about 0.01-20% by weight of the marine oil, preferably in the range 0.01-5%, more preferably in the range 0.01-1%, even more preferably in the range 0.01-0.1%, most preferably about 0.1%. In one embodiment, there is more than one tocopherol in the mixture; particularly preferred is a mixture containing α-tocopherol, β-tocopherol, γ-tocopherol and δ-tocopherol. One example of such a mixture is Tocoblend L 70 IP from Vitablend. In another embodiment, γ-tocopherol is the only tocopherol present in the composition.

By the expression "rosemary extract or an active fraction thereof" there is meant any extracts obtainable from rosemary which have antioxidant activity. Antioxidant activity might be measured by a number of methods such as the Oxipres method disclosed in example 2.

It is preferred that said rosemary extract is an oil-soluble extract. Such rosemary extracts are commercially available from a variety of manufacturers. The preferred antioxidant fraction of the extract are primarily in the dehydroabeitic acid class of diterpenes. Among the specifically identified active ingredients of the extract are carnosol, carnosic acid and rosmanol. Thus, in one embodiment said extract, or an active fraction thereof, comprises carnosol, carnosic acid or rosmanol or any mixture thereof. However, there are other unidentified components of the extract which also possess antioxidant activity, and these may also be used in the composition.

One of the preferred rosemary extract is one which contains from about 1-5% (w/w) carnosic acid, from about 2-7% (w/w) carnosol, and from about 0.11-0.5% (w/w) rosmanol; such an extract is commercially available under the tradename StabexE, from SKW Chemicals. An extract of this type can be used in an amount of from about 0.0001 to about 1%, preferably about 0.1-0.5% by weight of the marine oil. Another preferred rosemary extract is an extract which is commercially available under the tradename Oleoresin Rosemary Herbalox® Brand, from Kalsec. Analysis of one batch of this extract showed it to contain approx. 4.1% carnosic acid, 0.61% carnosol and 0.034% rosmarinic acid. An extract of this type can be used in an amount of from about 0.0001 to about 1%, preferably about 0.1-0.5%, more preferably about 0.2-0.4%, e.g about 0.3% by weight of the marine oil. Alternatively one or more of the compounds carnosic acid, carnosol and/or rosmarinic acid may be added, preferably in a combined concentration from about 0.00005 to about 0.05%, preferably about 0.005-0.03%, more preferably about 0.01-0.02 by weight of the marine oil. Canosic acid is the preferred compound to be added.

The composition according to the present invention further comprises ascorbic acid and/or an ascorbic acid derivative. By the expression "ascorbic acid derivative" there is meant any derivative of ascorbic acid such as e.g. ascorbyl palmitate and ascorbyl stearate. Preferably said ascorbic acid and/or ascorbic acid derivative is ascorbyl palmitate. One example of a commercially available ascorbyl palmitate product is Grindox ascorbyl palmitate from Danisco.

Preferably, said composition comprises ascorbic acid and/or an ascorbic acid derivative in the range of 0.04-0.12% by weight of the marine oil, more preferably in the range 0.06-0.10%, even more preferably in the range 0.07-0.08%.

By the expression "green tea extract or an active fraction thereof" there is meant any extracts obtainable from green tea which have antioxidant activity. Antioxidant activity might be measured by a number of methods such as the Oxipres method disclosed in example 2.

The antioxidant effect provided by green tea has primarily been attributed to the polyphenol content of the tea leaves, commonly known as tea catechins. The major tea catechins are epigallocatechin gallate (EGCG), epigallocatechin (EGC), epicatechin gallate (ECG), and epicatechin (EC). Of these, EGCG is the most abundant and possesses the most potent antioxidative activity.

Thus, it is preferred that said green tea extract, or an active fraction thereof, comprises at least one catechin, more preferably the green tea extract comprises epigallocatechin gallate (EGCG), epigallocatechin (EGC), epicatechin gallate (ECG), epicatechin (EC) or any mixture thereof, and even more preferably it comprises epigallocatechin gallate (EGCG).

It is preferred that the total amount of catechin(s) in said green tea extract, or an active fraction thereof, is as high as possible, e.g. in the range 1-80%, in the range 10-70%, in the range 20-50% or in the range 20-30% by weight of the extract.

Further, it is preferred that said green tea extract is added to a carrier. In one preferred embodiment said carrier is a polysaccharide, even more preferably said carrier is maltodextrin. The amount of said carrier is preferably in the range 50-95%, more preferably in the range 60-90%, even more preferably in the range 70-90%, most preferably about 80% by weight of the extract. Such an extract is commercially available under the tradename GUARDIAN™ Green Tea Extract 20M, from Danisco. An extract of this type can be used to prepare compositions according to the present invention in an amount of from 0.001 to 5% by weight of the marine oil, preferably in the range 0.002 to 1%, more preferably in the range 0.1 to 0.8% such as in the range 0.44 to 0.64%.

There are a number of commercial antioxidant formulations suitable for improving oxidative stability of a marine oil, one of them being Tocoblend ATR. The latter, produced by the company Vitablend, is a commercial liquid antioxidant formulation containing the following ingredients: ascorbyl palmitate, natural mixed tocopherols, natural rosemary extract, polysorbate 80 and monopropylene glycol.

In order to compare Tocoblend ATR with the composition of the present invention, four formulation were made with the same batch of an omega-3-acid triglyceride concentrate (EPAX 6000TG, batch no. 2080630) complying with the European Pharmacopoeia monograph 1352, Omega-3-acid triglycerides (example 5). While the preparation based on the composition according to the present invention (preparation B) appeared as a suspension of finely divided particles before filtration, the preparation based on Tocoblend ATR (preparation D) formed sticky lumps of solids which did not disperse in the oil upon heating.

It is assumed that polysorbate 80 and/or monopropylene glycol in some manner interfere with the surface of the maltodextrin particles, resulting in some form of agglomeration which reduces the solubilisation of the green tea extract. Surprisingly, in Preparation B (examples 5) no such agglomeration occur, giving a product that is far better stabilised against oxidation.

In order to investigate this further, several commercially available emulsifiers and/or antioxidant formulations containing such emulsifiers were tested as additives in the preparation of compositions according to the present invention (example 6).

Surprisingly, these experiments indicate that the present invention has best effect when avoiding the common food additives like lecithin and polysorbate 80/monopropylene glycol. Contrary to expectations, a formulation with polysorbate 80/propylene glycol reduced the solubilisation of green tea extract. Other emulsifying agents, including the commonly used lechitin, increased problems with precipitation during storage of oil samples. On the other hand, the citric acid emulsifier gave excellent results in combination with a formulation according to the present invention.

Thus, in one preferred embodiment the composition of the present invention further comprises citric acid ester of mono- and diglycerides. The skilled person will realise that other food additives/emulsifiers also may have similar effects as the citric acid based emulsifier.

As previously discussed, the antioxidant effect of green tea has primarily been attributed to the polyphenol content of the tea leaves, commonly known as tea catechins. Based on the assumption that the active components of green tea extract to a large extent are present as compounds like phenols, the dissolved amount may be analysed by titration with potassium hydroxide. This approach has been used in order to investigate whether the amount of monoglycerides, diglycerides and triglycerides in the oil may affect dissolution of the green tea components (example 7, FIG. 3).

The results clearly indicates that when green tea extract on maltodextrin carrier is added according to the present invention to a ethyl ester or triglyceride oil containing partial glycerides (mono- and diglycerides), the green tea components that can be analysed by titration with potassium hydroxide can be dissolved nearly quantitatively in the oil. For a triglyceride with very low amounts of partial glycerides the dissolution is much lower. This positive dissolution promoting effect of the partial glycerides (mono- and diglycerides) is very surprising.

In one embodiment according to the present invention, said marine oil preferably contains at least 3% partial glycerides (mono- and diglycerides) by weight of the marine oil, more preferably at least 5% partial glycerides (mono- and diglycerides) by weight of the marine oil, even more preferably at least 6% partial glycerides (mono- and diglycerides) by weight of the marine oil and most preferably at least 7% partial glycerides (mono- and diglycerides) by weight of the marine oil, such as e.g. at least 8, 10, 12, 15, 17, 19, 21, 23, 25, 30, 35, 40, 45, 50, 55, 60, 65 or 70% partial glycerides (mono- and diglycerides) by weight of the marine oil.

In one embodiment, at least 0.1 mg potassium hydroxide is required to neutralise 1 gram of the composition, more preferably at least 0.15 mg potassium hydroxide is required to neutralise 1 gram of the composition, even more preferably at least 0.2 mg potassium hydroxide is required to neutralise 1 gram of the composition and most preferably at least 0.25 mg potassium hydroxide is required to neutralise 1 gram of the composition.

In one embodiment, the composition according to the present invention comprises at least 0.05 mg catechins per gram oil (such as e.g. at least 0.06, 0.08, 0.1, 0.15, 0.2, 0.25, 0.3, 0.35, 0.4 or 0.45 mg catechins per gram oil), more preferably at least 0.5 mg catechins per gram oil (such as e.g. at least 0.55, 0.6, 0.65, 0.7, 0.75, 0.8, 0.85, 0.9 or 0.95 mg catechins per gram oil), even more preferably at least 1 mg catechins per gram oil (such as e.g. at least 1.05, 1.1, 1.15, 1.2, 1.25, 1.3, 1.35, 1.4 or 1.45 mg catechins per gram oil), most preferably at least 1.5 mg catechins per gram oil (such as e.g. at least 1.6, 1.8, 2, 2.2, 2.4, 2.6, 2.8, 3 or 4 mg catechins per gram oil). Said mg catechins per gram oil being analysed and calculated as set forth in example 7 and FIG. 3.

The invention will now be described further with reference to the following non-limiting examples.

EXAMPLES

Example 1

Preparation of Transparent Oil Samples Having Improved Oxidative Stability

Preparation 1 (Ascorbyl Palmitate, Tocopherols and Rosemary Extract)

Ascorbyl palmitate (Grindox, Danisco) was milled to obtain a finely divided powder and mixed with tocopherol (Tocoblend L 70 IP, Vitablend), rosemary extract (Herbalox® Brand, type O, NS, Kalsec) and olive oil (Ybarra Virgin) by stirring at 50° C. for ½ hour. The weight ratio of the ingredients was ascorbyl palmitate (13.3%), tocopherol (19.1%), rosemary extract (53.2%) and olive oil (14.4%). 5.4 mg/g (mg per gram marine oil) of the combined ingredients were added to a marine oil (EPAX 6000 TG EPAX) by stirring at 80° C. for 20 minutes.

Preparation 2 (Green Tea Extract)

5.4 mg/g (mg per gram marine oil) of a green tea extract (GUARDIAN™ Green Tea Extract 20M, Danisco) was stirred in a marine oil (EPAX 6000TG, EPAX) under heating at 80° C., and filtered while hot through a filter having a pore size in the range 15-40 μm.

Preparation 3 (Cold Filtration)

5.4 mg/g of the combined ingredients as described in Preparation 1 and 5.4 mg/g of green tea extract were mixed with the same marine oil by stirring at 80° C. for 20 minutes. The preparation was cooled to 20° C. and filtered through a filter having a pore size in the range 15-40 μm.

Preparation 4 (Hot Filtration)

5.4 mg/g of the combined ingredients as described in Preparation 1 and 5.4 mg/g of green tea extract were mixed with the same marine oil by stirring at 80° C. for 20 minutes. The preparation was filtered at 80° C. through a filter having a pore size in the range 15-40 μm.

Example 2

Oil Samples Having Improved Oxidative Stability (Oxipres Method)

The stability of the oils prepared in example 1 were tested by logging the pressure as a function of residence time at 50°

C. and an oxygen pressure of about 3.5 bars. (Oxipres apparatus produced by Microlab, Aarhus, Denmark)

All preparations showed significant improved stability compared to the pure oil without any antioxidants. The induction time for Preparation 1 and Preparation 2 was 115 and 124 hours, respectively (FIG. 1). Preparation 3 (278 hours) showed less stability than Preparation 4 (302 hours) (FIG. 1).

Thus, the inventors of the present invention have found a synergistic antioxidative effect from combining a mixture of tocopherols, rosemary extract and ascorbyl palmitate with green tea extract.

Example 3

Green Tea Extract with or without a Carrier

In Preparation 2 (example 1), a commercially available green tea extract which contains maltodextrin was used. In order to check whether maltodextrin is of importance or not, an analysis similar to what was done in example 2 was conducted using a commercially available green tea extract that does not contain a carrier (Indena™ Green Tea Extract). For comparison, the preparations were adjusted to contain the same amount of active ingredients. Even though the composition containing GUARDIAN™ Green Tea Extract 20M was shown to be more stable than the composition containing Indena™ Green Tea Extract, both products where demonstrated to be significantly more stable than the product which has not been mixed with green tea extract (data not shown). Further, maltodextrin alone does not affect the stability of the marine oil (Epax 6000TG oil, EPAX).

Example 4

Oil Samples Having Improved Oxidative Stability (Weight Increase Experiments)

Preparations similar to those described in Example 1 were made by using another marine oil, EPAX 6000 EE.

Figure 2:
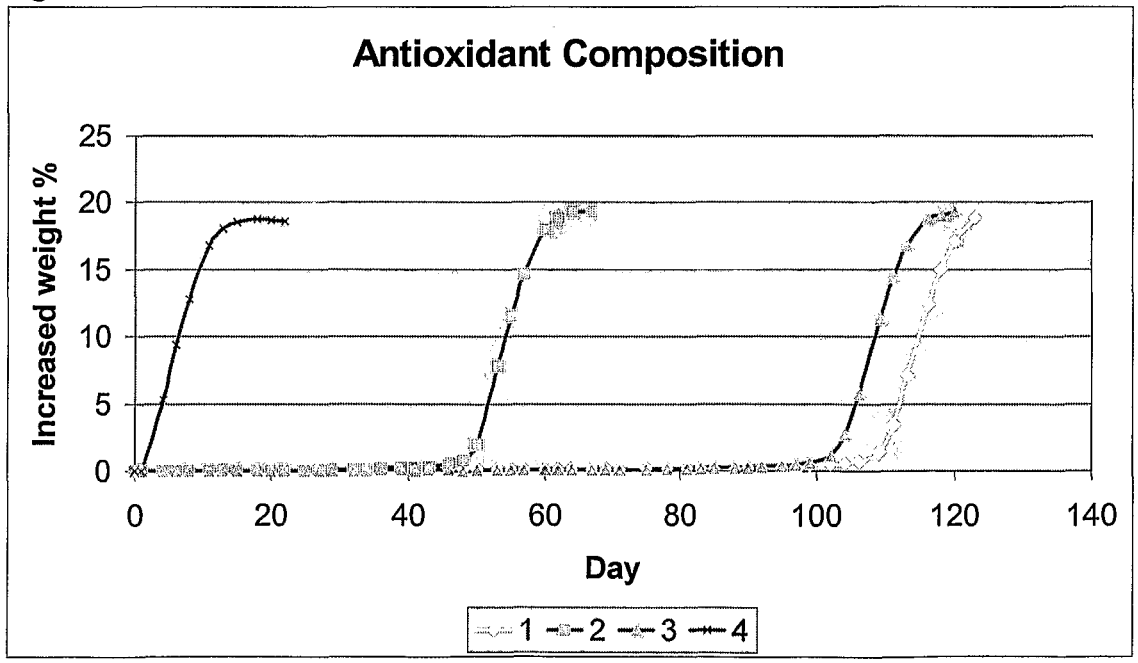
FIG. 2 shows a synergistic antioxidative effect (increased weight analysis) from combining a mixture of tocopherols (Tocoblend L 70 IP, Vitablend (1.03 mg per gram marine oil)), rosemary extract (Oleoresin Rosemary, Kalsec (2.87 mg per gram marine oil)) and ascorbyl palmitate (Grindox ascorbyl palmitate, Danisco (0.72 mg per gram marine oil)) and olive oil (0.78 mg olive oil per gram marine oil) with green tea extract (GUARDIAN™ Green Tea Extract 20M, Danisco (5.4 mg per gram marine oil before filtration).
1 represents 2+Green Tea Extract, "filtration, 80° C.";
2 represents 4+Ascorbyl Palmitate+Tocopherols+Rosemary extract;
3 represents 2+Green Tea Extract, "filtration, 20° C.";
4 represents EPAX 6000 EE.

Samples (3.0 gram) are stored in Petri dishes (diameter 6 cm) and incubated in a cabinet at 30° C., ambient relative humidity. The increase in weight (%), as a result of oxidation, is plotted as a function of residence time (FIG. 2). The time span from start of the experiment to the point where the curve rises steeply, is defined as the induction time.

As can be seen (FIG. 2), the three preparations containing antioxidants are much more stable than the pure fish oil. However, the two preparations containing green tea extract is far more stable than the sample without green tea extract. In accordance with example 2, the inventors of the present invention have found a synergistic antioxidative effect from combining a mixture of tocopherols, rosemary extract and ascorbyl palmitate with green tea extract.

Example 5

Comparison with a Commercial Antioxidant Formulation (Oxipres Method)

Preparation A (Ascorbyl Palmitate, Tocopherols and Rosemary Extract)

Ascorbyl palmitate (Grindox, Danisco) was milled to obtain a finely divided powder and mixed with tocopherol (Tocoblend L 70 IP, Vitablend), rosemary extract (Herbalox® Brand, type O, NS, Kalsec) and olive oil (Ybarra Virgin) by alternately magnetic stirring and immersing in a ultrasonic bath at 65° C. for 15 minutes. The weight ratio of the ingredients was ascorbyl palmitate (13.3%), tocopherol (19.1%), rosemary extract (53.2%) and olive oil (14.4%). 5.4 mg/g (mg per gram marine oil) of the combined ingredients were added to a marine oil (EPAX 6000 TG EPAX) by stirring at 80° C. for 20 minutes.

Preparation B (Ascorbyl Palmitate, Tocopherols, Rosemary Extracts and Green Tea Extract)

Preparation B was prepared identical to Preparation 4 in Example 1.

Preparation C (Tocoblend ATR[1])

5.4 mg/g (mg per gram marine oil) of Tocoblend ATR[1] was added to a marine oil (EPAX 6000 TG EPAX).

Preparation D (Tocoblend ATR[1] and Green Tea Extract)

Preparation D was identical to preparation C, except that green tea extract was added in the same manner and in the same concentration as in Preparation B.

[1]Tocoblend ATR

Tocoblend ATR, produced by the company Vitablend, is a commercial liquid antioxidant formulation containing the following ingredients: ascorbyl palmitate, natural mixed tocopherols, natural rosemary extract, polysorbate 80 and monopropylene glycol.

The stability of the oil preparations (A-D) were tested by the Oxipres method under exactly the same conditions as described in example 2.

The induction time for Preparation A and Preparation B was 117 and 315 hours, respectively, while the induction time for Preparation C and Preparation D was 74 and 89 hours, respectively.

These results demonstrate that an antioxidant composition according to the present invention gives far better protection of omega-3-acid triglycerides than the commercial formulation Tocoblend ATR, also when the latter is combined with green tea dissolved from a carrier according to the present invention.

Example 6

Effect of Emulsifiers

Lecithin

Addition of lecithin (l-α-lecithin, 3-sn-phosphatidylcholine from soy beans, Fluka) when making an antioxidant preparation as described in Preparation 1, Example 1 (relative weight of ascorbyl palmitate:lechitin=1:1) resulted in a product with a margarine like appearance. Although this formulation appeared less homogenous, and was more complicated to handle than the preparation 1 of Example 1, the formulation with lechitin was added to an omega-3 concentrate complying with the European Pharmacopoeia monograph 2063, Omega-3-acid ethyl esters 60.

Then green tea on maltodextrin was added under identical conditions as described in Preparation 4, Example 1. When stored in a refrigerator, precipitation of the oil was observed after only 6 days, making this preparation unsuitable for practical use. Similar precipitation, also after 6 days, was observed when the same oil, but with no addition of green tea, was stored in a refrigerator. When stored at room temperature, precipitate was formed after 6 days in the oil with green tea, and after 14 days in the oil without green tea.

Although lecithin is supposed to be a suitable additive in order to dissolve ascorbyl palmitate, this Example surprisingly show that a preparation without lecithin is preferable for making compositions according to the present invention.

Diacetyl Tartaric Acid Ester

An identical experiment was performed to that described for lecithin above, except that instead of lecithin a similar amount of the emulsifier Panodan® Visco-LO 2000, Danisco (diacetyl glycerides of tartaric acid made from sunflower oil) was utilised. The antioxidant formulation (including separate addition of green tea on a maltodextrin carrier according to the present invention) was added to an omega-3 concentrate complying with the European Pharmacopoeia monograph 2063, Omega-3-acid ethyl esters 60. Both when stored at room temperature and in refrigerator a precipitate was observed in the oil after only 6 days.

Rosemary Extract Containing Diacetyl Tartaric Ester

An antioxidant formulation was prepared identical to Preparation 4 in Example 1, except that the rosemary extract was substituted with Rosemary extract liquid refined, containing the emulsifier diacatyl acid ester of mono and diglycerides (E472e) (Vitablend, article no. 51310). This antioxidant formulation was added to an omega-3 concentrate complying with the European Pharmacopoeia monograph 2063, Omega-3-acid ethyl esters 60. A precipitate occurred after storage in refrigerator for 7 days, indicating that even small amounts of the emulsifier diacetyl tartaric ester is negative for the applicability of antioxidant formulations according to the present invention.

Acetic Acid Ester of Monoglycerides

Two identical experiments were performed to that described for diacetyl tartaric acid ester above, except that instead of diacetyl tartaric acid ester similar amounts of two commercial acetic acid esters of monoglycerides from hydrogenated palm based oil were used; the two acetic acid esters of monoglycerides had a degree of acetylation of 0.5 and 0.7 respectively. In both cases precipitate was observed after storage for 6 days, both at room temperature and in refrigerator.

Citric Acid Ester of Mono- and Diglycerides

An identical experiment to that with acetic acid ester of mono- and diglycerides from hydrogenated palm oil were performed, except that instead of acetic acid ester the emulsifier Grinsted® Citrem 2-IN-1 cosher, Danisco was used. The product consists of a neutralised citric acid ester of mono-diglyceride in powder form. The formulation was added to two different batches of omega-3 concentrates complying with the European Pharmacopoeia monograph 2063, Omega-3-acid ethyl esters 60. When the experiments were ended, the oils had been stored at room temperatures at 11 weeks without formation of any visible precipitate.

Example 7

Effects of Partial Glycerides

The antioxidant effect of green tea has primarily been attributed to the polyphenol content of the tea leaves, commonly known as tea catechins. Based on the assumption that the active components of green tea extract to a large extent are present as compounds like phenols, the dissolved amount may be analysed by titration with potassium hydroxide.

Preparation EE1

0, 0.5, 1, 2, 4, 5.4, 6, 7 and 8 mg/g (mg per gram marine oil) of a green tea extract (GUARDIAN™ Green Tea Extract 20M, Danisco) was stirred in a marine oil (5.6% triglycerides (TG); 3.0% diglycerides (DG); 3.6% monoglycerides (MG); 87.8% Ethyl esters/Free fatty acids (EE/FFA)) under heating at 80° C., and filtered while hot through a filter having a pore size in the range 15-40 μm.

Preparation of EE2

0, 0.5, 1, 2, 4, 5.4, 6, 7 and 8 mg/g (mg per gram marine oil) of a green tea extract (GUARDIAN™ Green TEA Extract 20M, Danisco) was stirred in a marine oil (0% triglycerides (TG); 0.5% diglycerides (DG); 12.0% monoglycerides (MG); 87.5% ethylesters/Free fatty acids (EE/FFA)) under heating at 80° C., and filtered while hot through a filter having a pore size in the range 15-40 μm.

Preparation TG1

3, 4, 5.4, 6, 7 and 8 mg/g (mg per gram marine oil) of a green tea extract (GUARDIAN™ Green Tea Extract 20M, Danisco) was stirred in a marine oil (93.6% triglycerides (TG); 4.9% diglycerides (DG); 0.4% monoglycerides (MG); 0.5% Ethyl esters/Free fatty acids (EE/FFA)) under heating at 80° C., and filtered while hot through a filter having a pore size in the range 15-40 μm.

Preparation TG2

0, 0.5, 1, 2, 3, 4, 5.4, 6, 7 and 8 mg/g (mg per gram marine oil) of a green tea extract (GUARDIAN™ Green Tea Extract 20M, Danisco) was stirred in a marine oil (63.9% triglycerides (TG); 31.6% diglycerides (DG); 1.9% monoglycerides (MG); 2.5% Ethyl esters/Free fatty acids (EE/FFA)) under heating at 80° C., and filtered while hot through a filter having a pore size in the range 15-40 μm.

Preparation Water 0, 0.5, 1, 2, 4, 5.4, 6, 7 and 8 mg/g (mg per gram water) of a green tea extract (GUARDIAN™ Green Tea Extract 20M, Danisco) was stirred in water at room temperature.

Preparation EE3

0, 0.5, 1, 2, 4, 5.4, 6, 7 and 8 mg/g (mg per gram marine oil) of a green tea extract (GUARDIAN™ Green Tea Extract 20M, Danisco) was stirred in a marine oil (0% triglycerides (TG); 0% diglycerides (DG); 0% monoglycerides (MG); 100% Ethyl esters/Free fatty acids (EE/FFA)) under heating at 80° C., and filtered while hot through a filter having a pore size in the range 15-40 μm.

The contents of partial glycerides are analysed by size-exclusion chromatography similar to the method described in Ph.Eur. monographs 1352 and 2063.

Compared with the other preparations (EE1, TG1 and TG2), EE3 was shown to have the lowest amount of dissolved catechines (data not shown).

Calculation of Dissolved Catechines 0, 0.5, 1, 2, 4, 5.4, 6, 7 and 8 mg/g (mg per gram water) of a green tea extract (GUARDIAN™ Green Tea Extract 20M, Danisco) was stirred in water at room temperature.

Each of the 9 samples is added potassium hydroxide until the composition is neutralised using phenolphthalein as indicator, cf. Ph.Eur. Monograph no. 2.5.1.Acid value.

Figure 3:
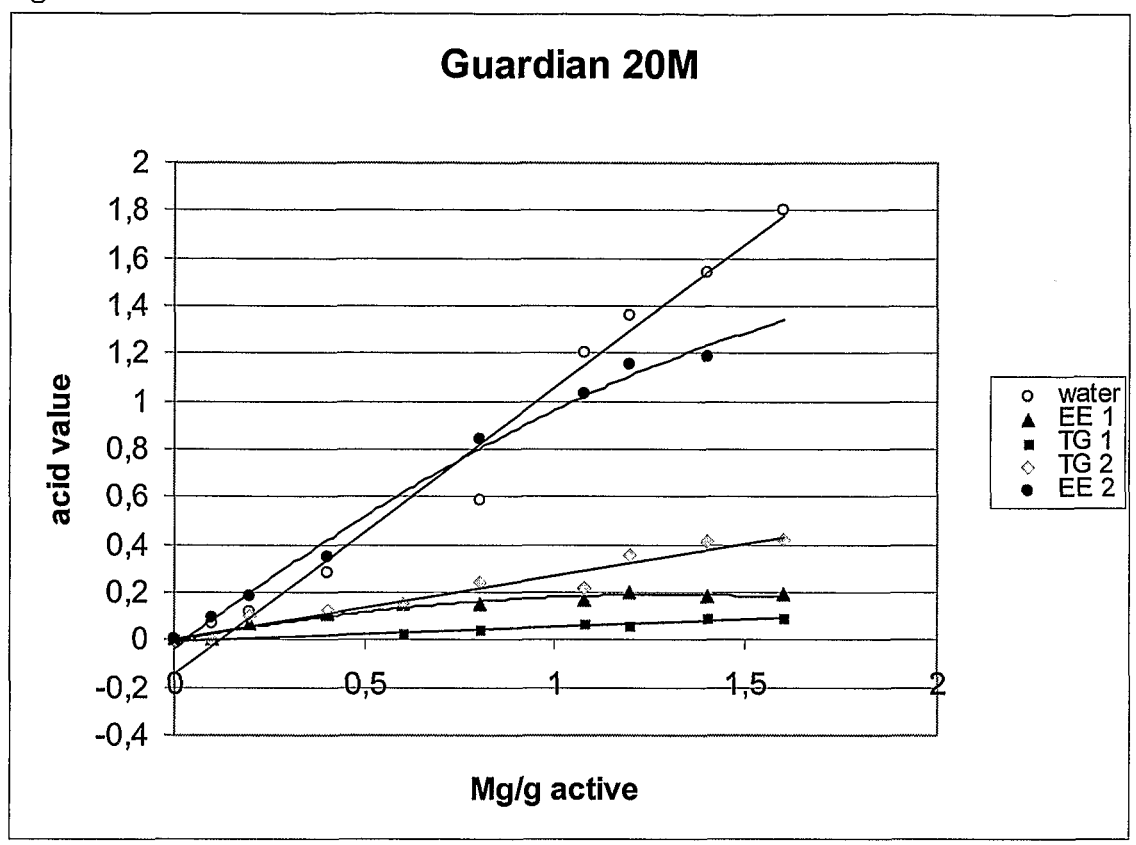
FIG. 3 shows the amount of green tea catechines dissolved in water and three different oil preparations. Dissolution in water gives a straight line that can be utilised as a calibration curve for estimation of the dissolved amount in the omega-3 containing oils.
Acid value number that expresses in milligrams the quantity of potassium hydroxide required to neutralise 1 gram of the oil.
Mg/g active amount of catechins per gram oil
Water Water+guardian 20M (green tea extract)
EE1 marine oil (5.6% triglycerides (TG); 3.0% diglycerides (DG); 3.6% monoglycerides (MG); 87.8% Ethyl esters/Free fatty acids (EE/FFA))+guardian 20M (green tea extract)
EE2 marine oil (0% triglycerides (TG); 0.5% diglycerides (DG); 12% monoglycerides (MG); 87.5% Ethyl esters/Free fatty acids (EE/FFA))+guardian 20M (green tea extract)
TG1 marine oil (93.6% triglycerides (TG); 4.9% diglycerides (DG); 0.4% monoglycerides (MG); 0.5% Ethyl esters/Free fatty acids (EE/FFA))+guardian 20M (green tea extract)
TG2 marine oil (63.9% triglycerides (TG); 31.6% diglycerides (DG); 1.9% monoglycerides (MG); 2.5% Ethyl esters/Free fatty acids (EE/FFA))+guardian 20M (green tea extract)

The amount of added catechines (5.4 mg GUARDIAN™ Green Tea Extract 20M contains about 1.08 mg catechines) is plottet on the X-axis and the amount of potassium hydroxide necessary to neutralise the composition is plottet on the Y-axis as shown in FIG. 3.

Dissolution in water gives a straight line that can be utilised as a calibration curve for estimation of the dissolved amount in the omega-3 containing oils.

The invention claimed is:

1. A stabilized marine oil composition comprising:
   a. a marine oil; and
   b. a stabilizer composition comprising:
      i. at least one tocopherol compound selected from the group consisting of alpha-tocopherol, beta-tocopherol, gamma-tocopherol, delta-tocopherol, 6-hydroxy-2,5,7,8-tetramethylchroman-2-carboxylic acid, tocopherol acetate, tocopherol linoleate, tocopherol nicotinate, tocopherol sorbate and tocopherol succinate;
      ii. at least one rosemary extract selected from the group consisting of carnosic acid, carnosol and rosmanol;

iii. at least one member of the group consisting of ascorbic acid, ascorbyl palmitate and ascorbyl stearate, wherein said at least one member is mixed with a vegetable oil, and wherein said vegetable oil is present in an amount of 1% or less (w/w) of the marine oil; and iv. a catechin component comprising (I) at least one catechin extracted from green tea, and (II) a carrier which comprises a polysaccharide;

wherein said composition does not comprise polysorbate 80, monopropylene glycol or lecithin.

2. The composition of claim 1 wherein the vegetable oil is olive oil.

3. The composition of claim 1 wherein the carrier in the catechin component is maltodextrin.

4. The composition of claim 1 wherein said marine oil is fish oil or a fish oil concentrate.

5. The composition of claim 1, wherein said tocopherol compound is selected is from the group consisting of α-tocopherol, β-tocopherol, γ-tocopherol and δ-tocopherol or any mixture thereof.

6. The composition of claim 1 wherein component b.iii is ascorbyl palmitate.

7. The composition of claim 1 wherein said catechin comprises epigallocatechin gallate (EGCG), epigallocatechin (EGC), epicatechin gallate (ECG), epicatechin (EC) or a mixture thereof.

8. The composition of claim 1 wherein said composition further comprises a citric acid ester of a mono- or diglyceride.

9. The composition of claim 1 wherein component b has been filtered through a filter having pore size in the range of 0.1-100 μm.

10. The composition of claim 1 wherein the marine oil contains at least 3% mono- and/or diglycerides by weight of the marine oil.

11. The composition of claim 1 wherein the amount of the tocopherol compound is in the range of from 0.01-20% by weight of the marine oil.

12. The composition of claim 1 wherein the amount of rosemary extract is in the range of from 0.0001-1% by weight of the marine oil.

13. The composition of claim 1 wherein the amount of component b.iii is in the range of from 0.04-0.12% by weight of the marine oil.

14. The composition of claim 1 wherein said composition comprises at least 0.1 mg catechin per gram marine oil.

15. The composition of claim 11 wherein component b has been filtered through a filter having pore size in the range of 10-40 μm.

16. A nutritional, food or pharmaceutical composition comprising the composition of claim 1.

* * * * *